(12) United States Patent
Fojtik

(10) Patent No.: US 12,390,203 B2
(45) Date of Patent: *Aug. 19, 2025

(54) ROTATIONAL DRIVE APPARATUS WITH RATCHETING MECHANISM

(71) Applicant: Distal Access, LLC, Park City, UT (US)

(72) Inventor: Shawn P. Fojtik, Park City, UT (US)

(73) Assignee: Distal Access, LLC, Park City, UT (US)

( * ) Notice: Subject to any disclaimer, the term of this patent is extended or adjusted under 35 U.S.C. 154(b) by 530 days.

This patent is subject to a terminal disclaimer.

(21) Appl. No.: 17/317,838

(22) Filed: May 11, 2021

(65) Prior Publication Data

US 2021/0332872 A1    Oct. 28, 2021

Related U.S. Application Data

(63) Continuation of application No. 16/513,581, filed on Jul. 16, 2019, now Pat. No. 11,002,346, which is a
(Continued)

(51) Int. Cl.
*A61B 17/00* (2006.01)

(52) U.S. Cl.
CPC ............... *A61B 17/00234* (2013.01); *A61B 2017/00367* (2013.01); *A61B 2017/00407* (2013.01)

(58) Field of Classification Search
CPC ............ F16H 19/02; A61B 10/02; A61B 2017/00407; A61B 2010/0208
See application file for complete search history.

(56) References Cited

U.S. PATENT DOCUMENTS

| 1,061,773 A | 5/1913 | Nahlinger |
| 1,290,489 A | 1/1919 | Bauer |

(Continued)

FOREIGN PATENT DOCUMENTS

| EP | 0702937 A1 | 3/1996 |
| JP | 2008-272488 A | 11/2008 |

(Continued)

OTHER PUBLICATIONS

European Patent Office, "Extended European Search Report," European Application No. 18748680.8, Nov. 6, 2020.
(Continued)

*Primary Examiner* — John R Downey
(74) *Attorney, Agent, or Firm* — DENTONS Durham Jones Pinegar

(57) ABSTRACT

A hand held, hand operated apparatus for rotating, or spinning, rotatably oscillating and/or inducing back and forth longitudinal movement in a device, such as an elongated medical device. A drive shaft of the hand held, hand operated rotational drive apparatus includes a ratcheting mechanism capable of enabling oscillating (repeated forward and reverse) rotation of a device that has been coupled thereto when there is little or no resistance on the rotated device, and of enabling an actuator to return to a position that will enable further forward, or driving, rotation of the drive shaft and the rotated device when resistance on the rotated device prevents the rotated device and the drive shaft from rotating in a reverse direction.

20 Claims, 6 Drawing Sheets

Related U.S. Application Data continuation of application No. 15/890,223, filed on Feb. 6, 2018, now Pat. No. 10,352,411.

(60) Provisional application No. 62/455,534, filed on Feb. 6, 2017.

(56) References Cited

U.S. PATENT DOCUMENTS

| | | |
|---|---|---|
| 5,397,340 A | 3/1995 | Nyman |
| 5,591,187 A | 1/1997 | Dekel |
| 5,911,722 A | 6/1999 | Adler et al. |
| 9,107,691 B2 | 8/2015 | Fojtik |
| 9,561,045 B2 | 2/2017 | Hinman et al. |
| 10,352,411 B2 | 7/2019 | Fojtik |
| 11,002,346 B2 | 5/2021 | Fojtik |
| 2007/0032808 A1 | 2/2007 | Anwar et al. |
| 2007/0282303 A1 | 12/2007 | Nash et al. |
| 2008/0097298 A1 | 4/2008 | Fisher et al. |
| 2008/0097402 A1 | 4/2008 | Hoganson et al. |
| 2008/0097465 A1 | 4/2008 | Rollins et al. |
| 2008/0255588 A1 | 10/2008 | Hinman |
| 2008/0277445 A1 | 11/2008 | Zergiebel et al. |
| 2008/0300574 A1 | 12/2008 | Belson et al. |
| 2009/0270862 A1 | 10/2009 | Arcenio |
| 2010/0249773 A1 | 9/2010 | Clark et al. |
| 2012/0095447 A1 | 4/2012 | Fojtik |
| 2016/0058485 A1* | 3/2016 | Staehler ............ A61B 17/8004 606/282 |

FOREIGN PATENT DOCUMENTS

| | | |
|---|---|---|
| JP | 2009-539567 A | 11/2009 |
| JP | 2014-500738 A | 1/2014 |
| WO | 2008045333 A2 | 4/2008 |

OTHER PUBLICATIONS

Japan Patent Office, "Reasons for Rejection," Japanese Application No. 2019-542589, Sep. 29, 2020.

USPTO as International Searching Authority, "International Search Report and Written Opinion", International Application No. PCT/US2018/017117, May 3, 2018.

* cited by examiner

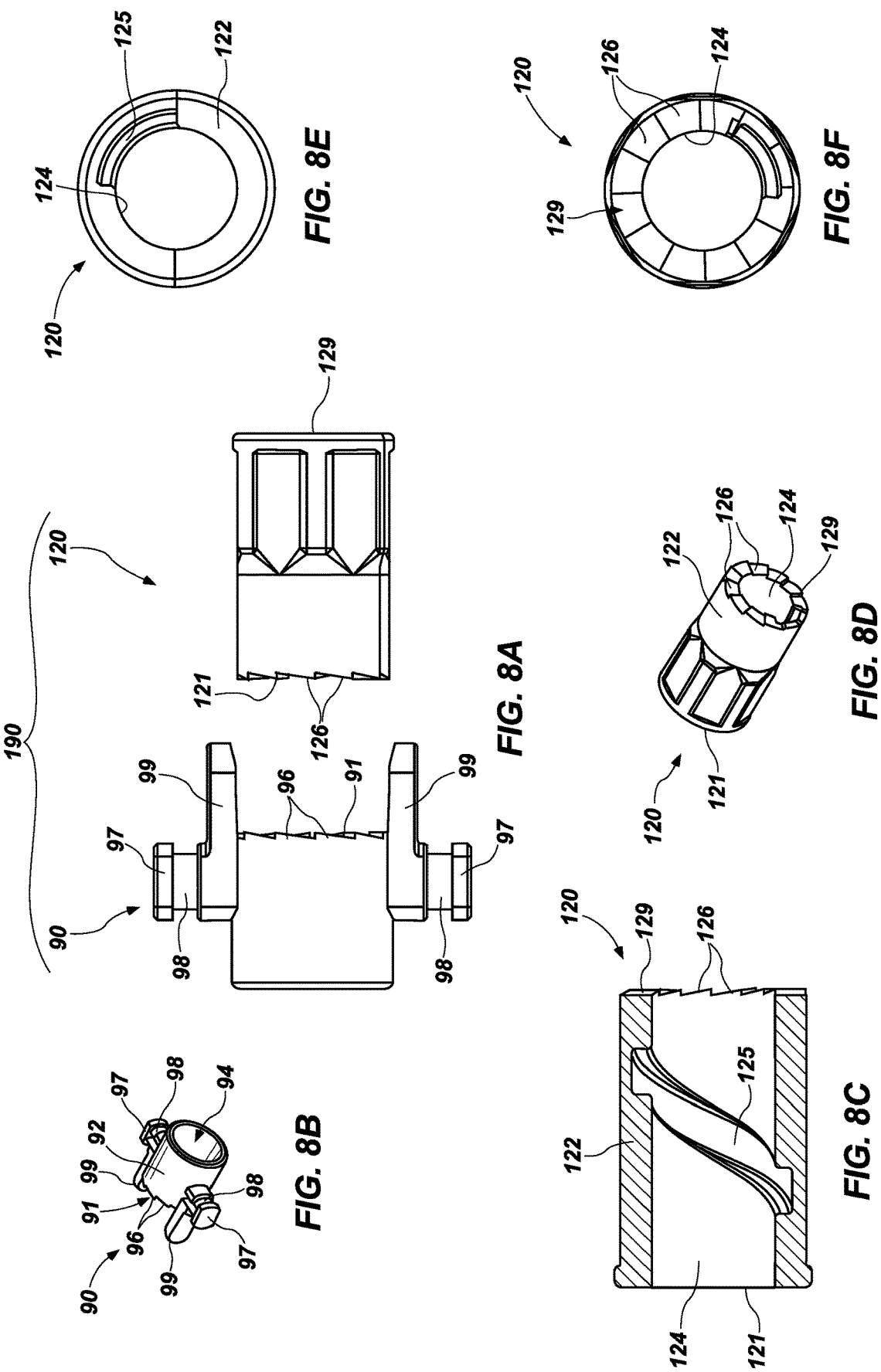

ROTATIONAL DRIVE APPARATUS WITH RATCHETING MECHANISM

CROSS-REFERENCE TO RELATED APPLICATIONS

This application is a continuation of U.S. patent application Ser. No. 16/513,581, filed on Jul. 16, 2019 and titled ROTATIONAL DRIVE APPARATUS WITH RATCHETING MECHANISM ("the '581 Application"), now U.S. Pat. No. 11,002,346, issued May 11, 2021, which is a continuation of U.S. patent application Ser. No. 15/890,223, filed on Feb. 6, 2018 and titled ROTATIONAL DRIVE APPARATUS WITH RATCHETING MECHANISM ("the '223 Application"), now U.S. Pat. No. 10,352,411, issued Jul. 16, 2019. The '223 Application includes a claim for the benefit of priority made pursuant to 35 U.S.C. § 119(e) to the Feb. 6, 2017 filing date of U.S. Provisional Patent Application No. 62/455,534, titled ROTATIONAL DRIVE APPARATUS WITH RATCHETING MECHANISM ("the '534 Provisional Application").

TECHNICAL FIELD

This disclosure relates generally to hand-held, hand-operated apparatuses and methods for rotating, or spinning, rotatably oscillating and/or inducing back and forth longitudinal movement in various devices, including, but not limited to, elongated medical instruments. More specifically, this disclosure relates to a hand-held, hand-operated rotational drive apparatus with a drive shaft that includes a ratcheting mechanism capable of enabling oscillating (repeated forward and reverse) rotation of a device that has been coupled thereto when there is little or no resistance on the rotated device, and of enabling an actuator to return to a position that will enable further forward, or driving, rotation of the drive shaft and the rotated device when resistance on the rotated device prevents the rotated device and the drive shaft from rotating in a reverse direction.

SUMMARY

In one aspect, the present disclosure includes various embodiments of an apparatus for causing an elongated medical instrument to rotate, or spin, about its longitudinal axis. Such an apparatus may be referred to herein as a "rooter." In a specific embodiment, a rooter includes a housing, a rotatable element within the housing, retention elements for securing the rotatable element in place relative to the housing, and an actuator capable of causing the rotatable element to rotate within the housing. The rotatable element may also be referred to as a "drive shaft." An apparatus according to this disclosure may also include a coupling element at (e.g., coupled to, etc.) a distal end of the rotatable element.

The actuator includes a ratcheting mechanism, which may enable rotation of the rotatable element in both directions (i.e., forward and reverse or clockwise and counterclockwise) about its longitudinal axis when less than a threshold rotational resistance is present on a rotated device, such as an elongated medical instrument, that has been coupled to the coupling element at the distal end of the rotatable element, and, thus, less than a threshold rotational resistance is present on the rotatable element. The ratcheting mechanism may also enable the actuator to return to a starting position from which the actuator can drive rotation of the rotatable element, even when the rotational resistance on the rotated device and/or the rotatable element equals or exceeds the threshold rotational resistance and, thus, prevents the rotated device and the rotatable element from oscillating, or from rotating in a direction (e.g., reverse, etc.) that would otherwise enable the actuator to return to its starting position.

The coupling element may be capable of engaging a specific type of device or any of a variety of different types of devices. Without limitation, the coupling element may be capable of engaging one or more different types of elongated medical instruments, such as a drill bit, a biopsy needle, a needle, a trocar, a cannula and/or stylet, a catheter, a wire, a macerator, or another elongated instrument that may be used to enable or effect a medical procedure within the body of a subject. In various embodiments, at least one end of the coupling element, which is accessible at or from a distal end of the housing of the apparatus, may be configured to receive and retain the device that is to be rotated.

The rotatable element may be disposed within an interior of the housing in a manner that enables the rotatable element to spin about its longitudinal axis. As the rotatable element rotates within the housing, which may remain substantially stationary (e.g., within a user's grasp, etc.), a device, such as an elongated medical instrument engaged by the coupling element may rotate. In some embodiments, the rotatable element may comprise an elongated member with a longitudinal axis, about which the rotatable element may rotate, or spin. In a more specific embodiment, the rotatable element may include a helical ridge that may enable the rotatable element to be rotationally driven.

An actuator may be associated with the rotatable element in such a way as to cause the rotatable element to rotate. In a specific embodiment, the actuator may include an external element configured for manual operation, as well as an internal element that interacts with the rotatable element. The actuator may be disposed around at least a portion of the rotatable element. In embodiments where the rotatable element has a helical ridge, the internal element of the actuator may be positioned between longitudinally adjacent locations of the helical ridge. In other embodiments, an actuator may include one or more grooves that are configured complementarily to and cooperate with the helical ridge. The actuator may move longitudinally relative to the rotatable element (e.g., in directions substantially parallel to the rotational axis of the rotatable element, etc.), while the internal element of the actuator and the helical ridge of the rotatable element interact with one another to cause the rotatable element, as well as any medical element engaged thereby, to rotate, or spin.

Longitudinal movement of the actuator relative to the housing may be enabled by one or more elongated slots that extend through the housing, along at least a portion of its length, and by one or more external elements and one or more intermediate elements of the actuator. Each intermediate element of the actuator may extend through a corresponding elongated slot. The corresponding external element of the actuator may be moved (e.g., manually, by way of an associated handle, with a motor, etc.) along at least a portion of the length of the elongated slot to drive movement of the actuator along a length of the rotatable element. In embodiments where the external element and/or the intermediate element pivot relative to the actuator, the axis about which such pivoting occurs may be oriented perpendicular to and extend through an axis about which the rotatable element rotates (e.g., a longitudinal axis of the rotatable element, etc.). This configuration may impart the rooter with stability and prevent binding as the actuator moves back and forth along the length of the rotatable element. The elongated slot may receive an intermediate element of the actuator, holding the actuator in place as it is moved along the length of the rotatable element.

The ratcheting mechanism of the actuator may enable the actuator to return to a starting position along the rotational element and, thus, enable further driving rotation of the rotational element, even when rotational resistance on a device that has been coupled to the coupling element prevents the rotated device and the rotational element from oscillating, or from rotating in reverse direction. In some embodiments, the ratcheting mechanism includes a distal member of the actuator, a proximal member of the actuator, and a biasing member (e.g., a spring, etc.). The distal member may be coupled to a movable element of a handle. The distal member may be capable of sliding along a length of the rotatable element without directly causing the rotatable element to rotate. The distal member may also include engagement features capable of engaging the proximal member and holding the proximal member rotationally stationary when the movable element of the handle forces the distal member in a proximal direction along the length of the rotatable element. As the proximal member is held rotationally stationary over the rotational element while it is forced in the proximal direction along the length of the rotatable element by the distal member, it may engage the rotational element in a manner that drives rotation of the rotational element (e.g., by receiving or engaging a helical ridge of a rotatable element, etc.). Upon releasing the movable element of the handle, the biasing member may force the proximal member and the distal member in a distal direction along the length of the rotatable element. If the force the biasing element exerts on the proximal member exceeds a rotational resistance on a rotated device that has been coupled to the coupling element (and, thus, to the rotational element), the proximal member may remain rotationally stationary over the rotatable element, distal movement of the proximal member of the ratcheting mechanism may drive the rotational element and the rotated device in a reverse direction, thus enabling oscillation of the rotatable element and of the rotated device. If the rotational resistance on the rotated device exceeds the biasing force the biasing member exerts on the proximal member, the engagement features of the proximal member may disengage corresponding engagement features on the distal member of the ratcheting mechanism, enabling the proximal member to rotate over the rotational element and, thus, enabling the biasing member to force the proximal member distally without limited rotation or no rotation of the rotatable element (i.e., the proximal member, rather than the rotatable element, may spin when the rotatable element moves distally), and forcing the distal member of the ratcheting mechanism and the moveable member of the handle distally as well.

This disclosure also includes systems for effecting rotational processes. A system of this disclosure includes a rooter, as well as a rotated device (e.g., an elongated medical instrument, etc.) capable of being coupled with the coupling element of the rooter. The rooter may be manually operable. As the rooter operates, it causes the rotated device to rotate or spin in a drive direction and, depending upon an amount of rotational resistance on the rotated device, it may cause the rotated device to spin in a reverse direction (which may enable oscillation of the rotated device). If at least a threshold amount of rotational resistance is present on the rotated device, the ratcheting mechanism may enable the rotational element and the rotated device to remain stationary, while enabling the proximal and distal members of the actuator and any moveable element of a handle associated therewith to return to a starting position.

In another aspect, methods for rotating, or spinning, devices (e.g., elongated medical instruments, etc.) are disclosed, as are methods for inducing oscillatory (i.e., alternating between clockwise and counterclockwise rotation) or vibration-like movement, longitudinal movement (e.g., a back-and-forth hammering action, etc.) and other types of movement in rotated devices. In such a method, an elongated medical instrument is associated with (e.g., engaged by, etc.) a coupling element of a rooter. Operation of an actuator of the rooter (e.g., manually, with a user's thumb or finger on a moveable element of a handle; with a motor; etc.) causes the rotatable element, along with the rotated device that has been secured in place relative to the rotatable element, to rotate or spin in a forward direction. The rotatable element may be rotated continuously in a single direction (e.g., clockwise or counterclockwise), or it may be rotated in an alternating or oscillating fashion (i.e., one direction, then another).

In embodiments where rotational resistance on the rotated device prevents it from rotating in a reverse direction (e.g., is equal to or greater than a threshold rotational resistance, etc.), the ratcheting mechanism of the rooter may enable the actuator (i.e., its proximal and distal members) to disengage and to return to their starting positions.

In some embodiments, movement of the rotatable element of a rooter and any elongated medical instrument coupled thereto may be accompanied by longitudinal movement of the rotatable element and any elongated medical instrument in one or more directions. When the rotatable element is oscillated, this longitudinal movement may include a repeated back-and-forth movement, inducing a hammering action in the rotatable element and any elongated medical instrument that has been coupled thereto. This hammering action may be used alone or in conjunction with oscillation of an elongated medical instrument to facilitate its introduction into or through a structure (e.g., a blockage, such as arterial plaque; a calcification; bone; etc.).

Other aspects, as well as features and advantages of various aspects, of the disclosed subject matter will become apparent to those of skill in the art from consideration of the ensuing description, the accompanying drawings, and the appended claims.

BRIEF DESCRIPTION OF THE DRAWINGS

In the drawings:

FIG. 8A is an exploded side view showing an embodiment of an actuator of a rooter according to this disclosure, including a distal member and a proximal member that may engage and disengage one another;

FIG. 8B is a perspective view of the distal member of the embodiment of actuator shown in FIG. 8A;

FIG. 8C is a cross-section through the proximal member of the embodiment of actuator shown in FIG. 8A;

FIG. 8D is a perspective view of the proximal member of the embodiment of actuator shown in FIG. 8A;

FIGS. 8E and 8F are end views of the proximal member of the embodiment of actuator shown in FIG. 8A;

DETAILED DESCRIPTION

Figure 1:
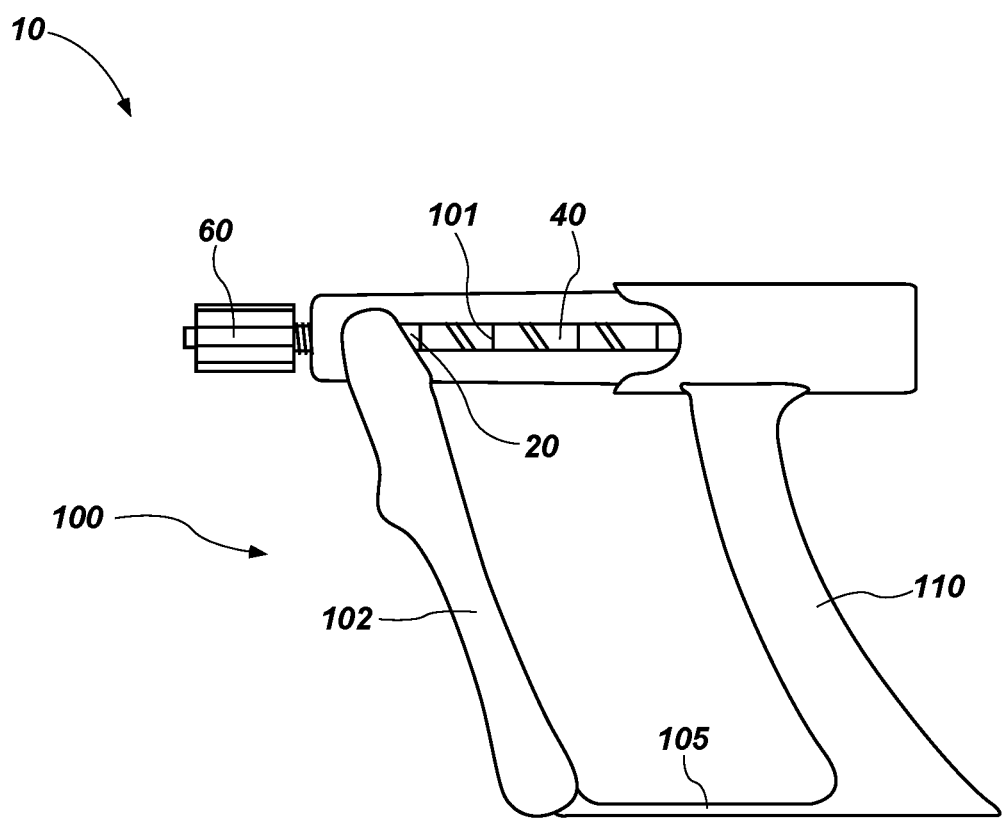
FIG. 1 depicts an embodiment of rooter of this disclosure.
Figure 2:
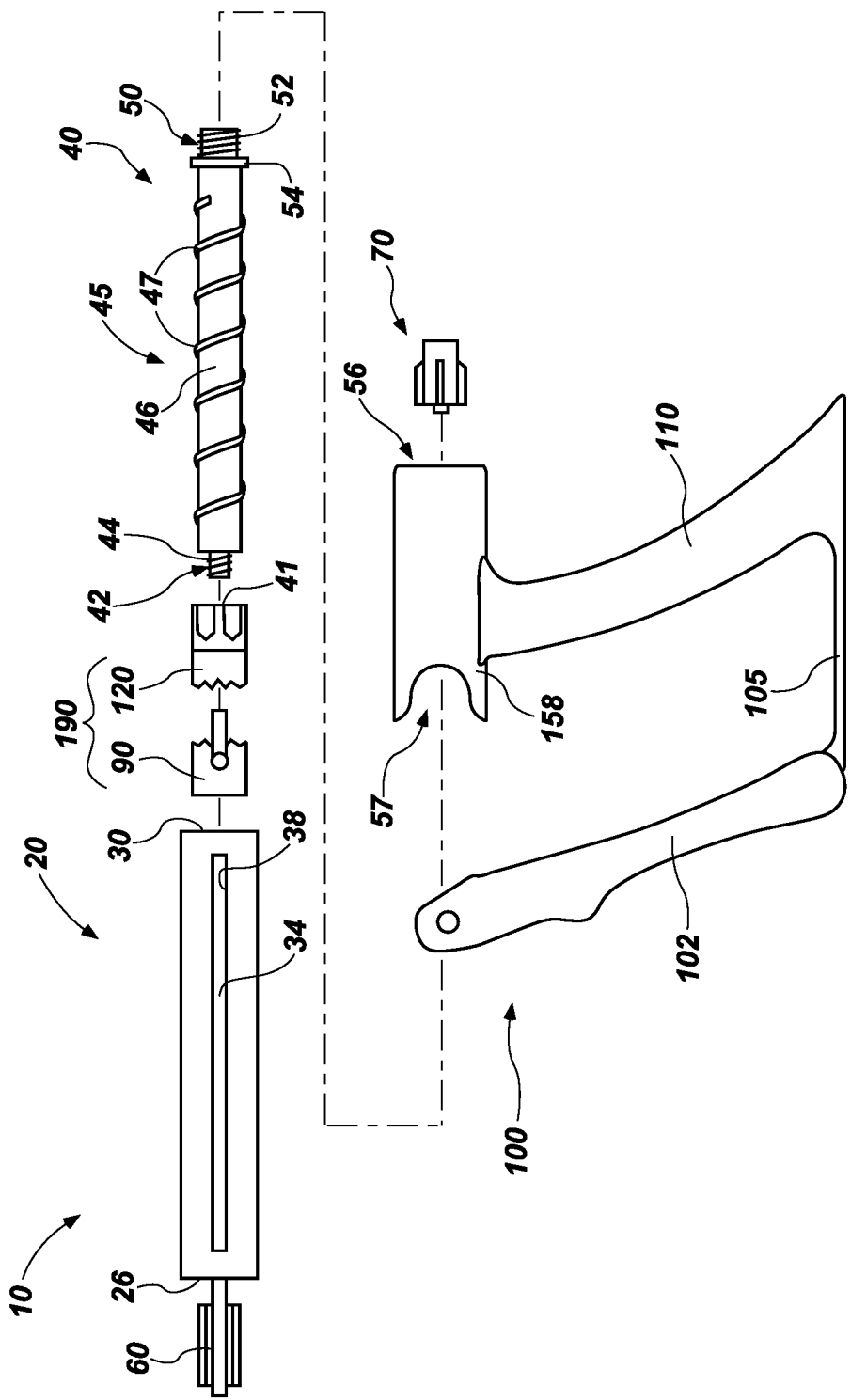
FIG. 2 is an exploded view of the embodiment of rooter shown by FIG. 1.

With reference to FIGS. 1 and 2, an embodiment of a rooter 10 that incorporates teachings of this disclosure is illustrated. The rooter 10 includes a housing 20, a rotatable element 40, a distal retention element 60 and a proximal retention element 70, and an actuator 90. Either or both of the distal retention element 60 and the proximal retention element 70 may couple a device that is to be rotated (e.g., an elongated medical instrument, etc), or a "rotated device," to the rotatable element 40; accordingly, the distal retention element 60 and the proximal retention element 70 may be referred to as a "coupling element."

Figures 3A, 3B, 3C:
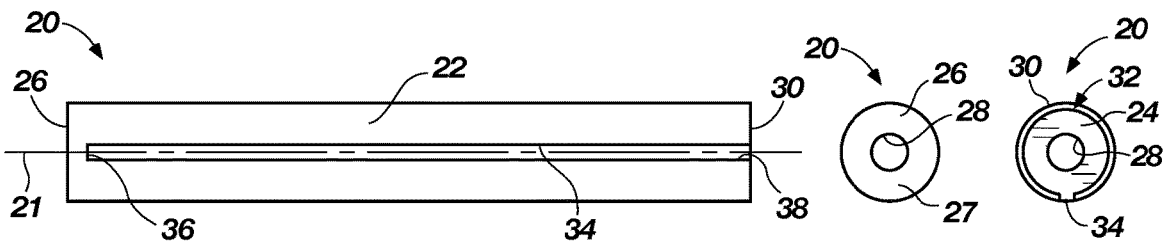
FIGS. 3A, 3B, and 3C are, respectively, bottom, distal end, and proximal end views of a housing of the embodiment of rooter depicted by FIGS. 1 and 2.

The housing 20, which is also shown in FIGS. 3A-3C, is an elongated element with an exterior 22 and a hollow interior 24. In the depicted embodiment, the housing 20 is cylindrical in shape, with a longitudinal axis 21 extending centrally through the length of the housing 20. The housing 20 includes a distal end 26 and an opposite, proximal end 30. A longitudinal slot 34 extends along a portion of the length of the housing 20.

The distal end 26, which is the end of the housing 20 that may be located farthest from an individual during use of the rooter 10 (FIGS. 1 and 2), is partially closed, as depicted by FIG. 3B. In a specific embodiment, the distal end 26 may include a circumferential lip 27 that defines an opening 28, which extends through the housing 20, from its exterior 22 to its interior 24. The opening 28 may be centered about the longitudinal axis 21 of the housing 20.

As seen in FIG. 3C, the proximal end 30 of the housing 20, which may be located closest to the individual during operation of the rooter 10, may include an opening 32 that exposes the interior 24 of the housing 20. In some embodiments, the proximal end 30 of the housing 20 may be configured to receive a cap 56 (FIGS. 5A-5C), which may at least partially close the opening 32 at the proximal end 30.

The longitudinal slot 34, illustrated in FIGS. 3A and 3C, extends through a wall of the housing 20, from the exterior 22 of the housing 20 to the interior 24 of the housing 20. In the embodiment depicted by FIG. 3A, the longitudinal slot 34 is substantially linear. A distal end 36 of the longitudinal slot 34 may be located adjacent to, but proximally spaced apart from, the distal end 26 of the housing 20. An opposite, proximal end 38 of the longitudinal slot 34 is located at or near (i.e., distally spaced apart from) the proximal end 30 of the housing 20.

Figures 4A, 4B, 4C:
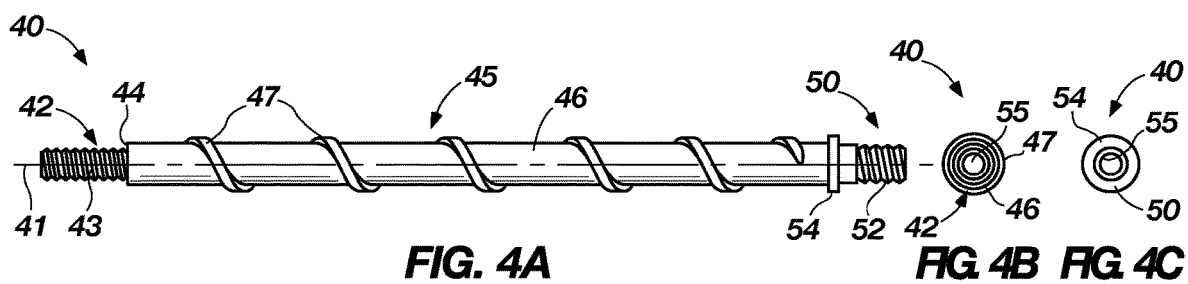
FIGS. 4A, 4B, and 4C are, respectively, side, distal end, and proximal end views of a rotatable element of the embodiment of rooter shown in FIGS. 1 and 2.

The rotatable element 40 of the embodiment of the rooter 10 (FIGS. 1 and 2) illustrated by FIGS. 4A-4C is an elongated element that is configured to be assembled with the housing 20 (FIGS. 3A-3C) of the rooter 10. In some embodiments, the rotatable element 40 may be tubular and, thus, include a conduit 55 extending through a portion of its length or through its entire length. A longitudinal axis 41 of the rotatable element 40 extends centrally or substantially centrally through a length of the rotatable element 40. In embodiments where the rotatable element 40 includes a conduit 55, the conduit 55 and the longitudinal axis 41 of the rotatable element 40 may be aligned (e.g., concentric, etc.).

In embodiments where the rotatable element 40 includes a conduit 55, the conduit 55 may enable flow communication between the interior of a hollow device (e.g., an elongated medical instrument, such as a needle, catheter, etc.) to be coupled to the rooter 10 and a separate flow facilitating apparatus (e.g., a syringe, an aspiration device, and infusion device, a vacuum line, etc.).

In some embodiments, the conduit 55 through the rotatable element 40 may be configured to receive the device. The conduit 55 may be configured in such a way that a portion of the device may extend partially or completely through a length of the rotatable element 40. In other embodiments, the conduit 55 may serve as an intermediate channel between the device and the flow facilitating apparatus.

In the depicted embodiment, the rotatable element 40 includes an intermediate portion 45, as well as a distal portion 42 and a proximal portion 50 at opposite ends of the intermediate portion 45.

The intermediate portion 45, which may be generally cylindrical in shape, includes a rotation facilitator. In the illustrated embodiment, the rotation facilitator comprises a helical ridge 47, which protrudes from an outer surface 46 of the intermediate portion 45. In particular, the helical ridge 47 may wrap circumferentially around the intermediate portion 45. The helical ridge 47 may be continuous, as illustrated, or it may comprise a discontinuous structure. The helical ridge 47 extends along at least a portion of the length of the intermediate portion 45. In some embodiments, the helical ridge 47 may extend along only a part of the intermediate portion 45, as in the depicted embodiment, where the ends of the helical ridge 47 are spaced apart from corresponding ends of the intermediate portion 45.

The pitch of the helical ridge 47 may be configured to impart the rooter 10 with a desired number of rotations per stroke (i.e., full movement of the actuator 90 along the length of the rotatable element 40). For example, a helical ridge 47 with a relatively large pitch may cause the rotatable element 40 to rotate more slowly, with greater torque, and with fewer revolutions per stroke (e.g., about 1½ revolutions per stroke, about 1 revolution per stroke, etc.) than a helical ridge 47 with a smaller pitch. When faster rotation or an increase in revolutions per stroke (e.g., five revolutions per stroke or more, etc.) is desired, the pitch of the helical ridge 47 may be decreased.

The helical ridge 47 may be configured in a manner that facilitates the use of certain processes in the manufacture of the rotatable element 40. For example, one or more surfaces of the helical ridge 47 may be flattened to facilitate the use of injection molding processes to manufacture the rotatable element 40.

Figures 7A, 7B, 7C:
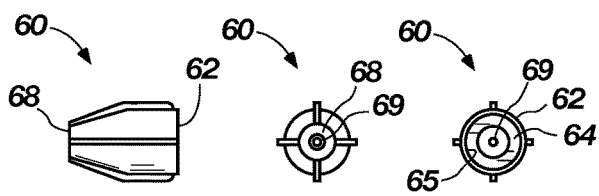
FIGS. 7A, 7B, and 7C are side, distal end, and proximal end views of a distal retention element of the embodiment of rooter illustrated by FIGS. 1 and 2.

The distal portion 42 of the rotatable element 40 may also be cylindrical in shape. In the embodiment shown in FIGS. 4A-4C, the distal portion 42 of the rotatable element 40 has a smaller diameter than the intermediate portion 45 of the rotatable element 40. Thus, a circumferential ledge 44 is present at the boundary between the distal portion 42 and the intermediate portion 45. The distal portion 42 may also be configured to pass through the opening 28 in the distal end 26 of the housing 20 (FIGS. 3A and 3C), and to protrude from the distal end 26. The distal portion 42 may be configured to engage or be engaged by the distal retention element 60 (FIGS. 7A-7C). In this regard, a distal portion 42 of some embodiments of a rotatable element 40 of a rooter 10 may include one or more retention features 43, such as the helical thread shown in FIG. 4A.

The proximal portion 50 of the rotatable element 40 may likewise have a cylindrical shape. In some embodiments, the proximal portion 50 may be configured to protrude beyond the proximal end 30 of the housing 20 of a rooter 10. The proximal portion 50 may be configured to engage or be engaged by the proximal retention element 70 (FIGS. 6A-6D). Such engagement may, in some embodiments, be at least partially enabled by at least one retention feature 52, such as the helical thread illustrated by FIG. 4A.

A circumferential rim 54, which extends around and protrudes from the outer portion 46 of the rotatable element 40, may delimit, or define a boundary between, the intermediate portion 45 of the rotatable element 40 and its proximal portion 50. The circumferential rim 54 may provide a stop for a proximal member 120 of an actuator 190 (FIGS. 8A-8D) that cooperates with the rotatable element 40 and is configured to cause the rotatable element 40 to rotate about its longitudinal axis 41.

Figures 5A, 5B, 5C, 6A, 6B, 6C, 6D:
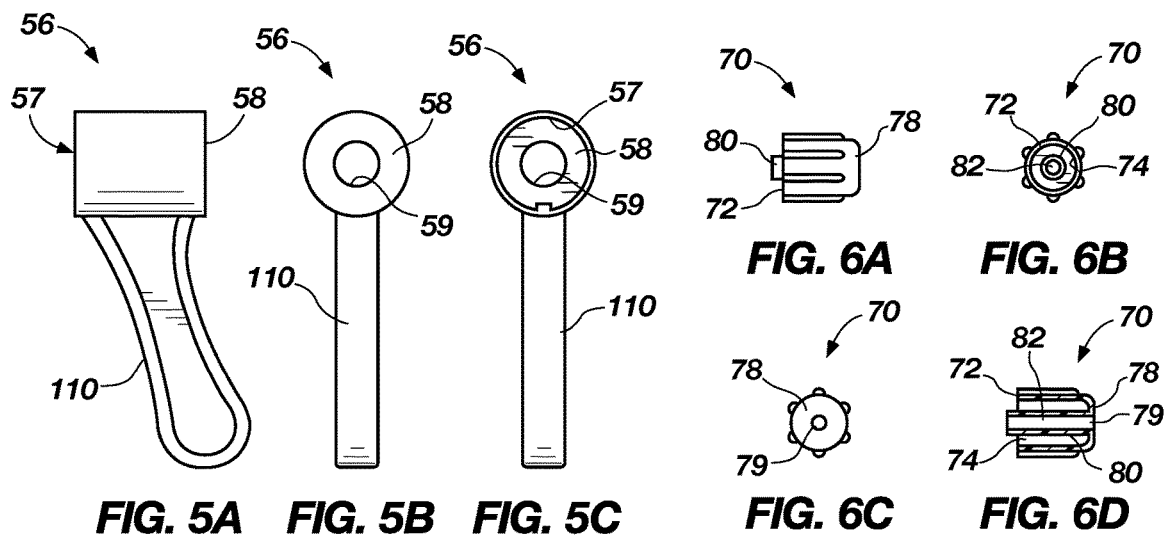
FIGS. 5A, 5B, and 5C are side, rear, and front views, respectively, of a cap of the embodiment of rooter illustrated by FIGS. 1 and 2.
FIGS. 6A, 6B, and 6C are, respectively, side, distal end, and proximal end views of a proximal retention element of the embodiment of rooter shown in FIGS. 1 and 2.
FIG. 6D is a cross-section taken through the length of the proximal retention element depicted by FIGS. 6A-6C.

In some embodiments, a rooter 10 (FIGS. 1 and 2) may include a cap 56 configured to cooperate with the circumferential rim 54 to retain the rotatable element 40 within the interior of the housing 20. An embodiment of the cap 56 that may be used as part of the rooter 10 (FIGS. 1 and 2) is shown in FIGS. 5A-5C. The cap 56 may be configured to be disposed over the opening 32 (FIGS. 3A and 3C) in the proximal end 30 of the housing 20. In a specific embodiment, the cap 56 may include a receptacle 57 that receives the proximal end 30 of the housing 20. An interior surface of an end 58 of the cap 56 may be configured to abut the circumferential rim 54 (FIGS. 4A and 4C) of the rotatable element 40 and an edge of the proximal end 30 of the housing 20, while an aperture 59 through the end 58 of the cap 56 may be configured to receive the proximal portion 50 of the rotatable element 40.

The cap 56 may, in some embodiments, be held in place on the proximal end 30 of the housing 20 by way of the proximal retention element 70, an embodiment of which is depicted in FIGS. 6A-6D. The proximal retention element 70 is configured to be coupled with the proximal portion 50 (FIGS. 4A and 4C) of the rotatable element 40. More specifically, the proximal retention element 70 may have the appearance of a cap, with an open distal end 72 and a receptacle 74 that are configured to receive the proximal portion 50 of the rotatable element 40. In addition, at an opposite end of the receptacle 74 from the open distal end 72, the proximal retention element 70 may have a substantially closed proximal end 78.

The receptacle 74 may be configured to engage or to be engaged by the proximal portion 50 (FIGS. 4A and 4C) of the rotatable element 40. In a specific embodiment, the receptacle 74 may include at least one retention feature (not shown), such as a helical thread on an interior surface of the receptacle 74, configured to mutually engage a corresponding retention feature 52 of the proximal portion 50 of the rotatable element 40.

An opening 79 may extend through the proximal end 78 of the proximal retention element 70. In some embodiments, such as that illustrated by FIGS. 6A-6D, the proximal retention element 70 and, in a particular embodiment, its opening 79 may be configured to receive and engage a device that is to be rotated. In the illustrated embodiment, the opening 79 through the proximal end 78 of the proximal retention element 70 communicates with a conduit 82 of a male member 80. The male member 80 extends through the receptacle 74 of the proximal retention element 70. When used with an embodiment of rotatable element 40 (FIGS. 4A-4C) that includes a conduit 55, the male member 80 of the proximal retention element 70 may be configured for insertion into the conduit 55.

In some embodiments, the proximal retention element 70 may be configured to engage a device that is to be rotated, such as an elongated medical instrument, in a manner that causes the device to rotate as the proximal retention element 70 rotates. For example, and not to limit the scope of this disclosure, the surfaces that define the opening 79 through the proximal end 78 of the proximal retention element 70 may be configured to lock onto, grasp, or engage a surface of the device. As another non-limiting example, the elongated retention element 70 may include one or more features (e.g., a retention slot, a locking feature, etc.) that communicate or are otherwise associated with the opening 79 through the proximal end 78 to enable selective locking, grasping, or other engagement of the surface of the device that is to be rotated. In yet another non-limiting example, the proximal retention element 70 may be configured to couple with a separate device (not shown) that locks onto, grasps, or otherwise engages the surface of the device that is to be rotated.

The distal retention element 60, an embodiment of which is illustrated by FIGS. 7A-7C, may also have the general appearance of a cap, with an open proximal end 62, an interior receptacle 64 that communicates with the proximal end 62, and a substantially closed distal end 68. The proximal end 62 and the receptacle 64 are configured to receive the distal portion 42 (FIGS. 4A and 4B) of the rotatable element 40. In some embodiments, the receptacle 64 includes one or more retention features (not shown), which may be configured to mutually engage a corresponding retention feature 43 of the distal portion 42 of the rotatable element 40, such as a helical thread carried by the surface 65 of the depicted receptacle 64.

The distal end 68 of the distal retention element 60 may include an opening 69, which may be configured to receive a device that is to be rotated, such as an elongated medical instrument. When such a distal retention element 60 is configured for assembly with an embodiment of rotatable element 40 (FIGS. 4A-4C) that includes a conduit 55 extending therethrough, the opening 69 through the distal end 68 of the distal retention element 60 may be configured for alignment and/or communication with the conduit 55.

In addition to being configured to receive a device that is to be rotated, some embodiments of distal retention elements 60 may be configured to lock onto, grasp, or otherwise engage, or at least partially engage, the device that is to be rotated. Without limiting the scope of this disclosure, a distal retention element 60 may include a locking element (not shown) at its distal end 68, external or internal (i.e., within the opening 69 in the distal end 68) threading, internal features (e.g., ribs, etc.) that lock onto, grasp, or otherwise engage an outer surface of the device, other locking features, or the distal retention element 60 may be configured to couple with a separate device (not shown) that locks onto, grasps, or otherwise engages the surface of the device that is to be rotated.

Figure 8G:
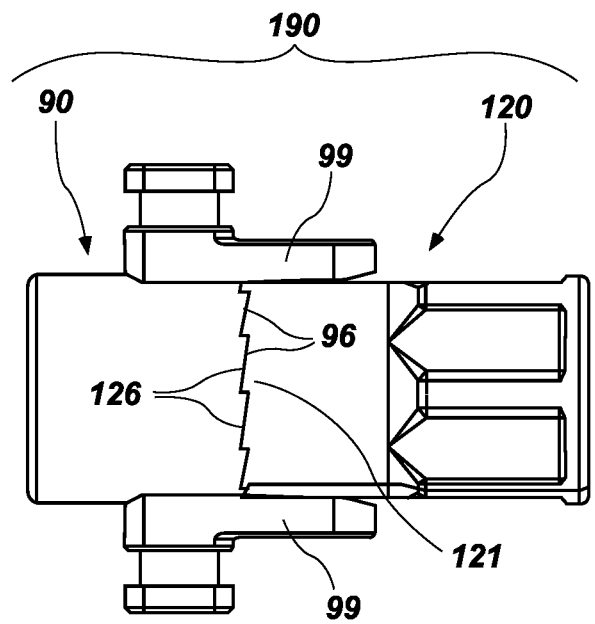
FIG. 8G shows the distal and proximal members of the embodiment of actuator of FIG. 8A in abutting, engaged positions.
Figure 9:
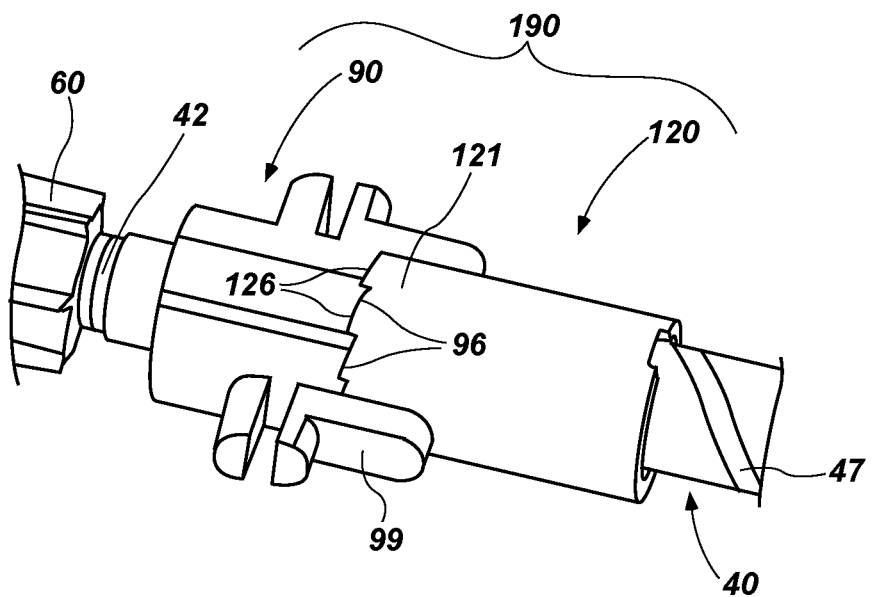
FIG. 9 shows the embodiment of actuator depicted by FIG. 8A in its starting position over a distal end of the rotational element of the embodiment of rooter illustrated by FIGS. 1 and 2.

Turning now to FIGS. 8A and 8G, an embodiment of an actuator 190 that may be used with the embodiments of the housing 20 and the rotatable element 40 shown in FIGS. 4A-4C is illustrated. In particular, the actuator 190 may include a distal member 90 and a proximal member 120.

In the depicted embodiment, with added reference to FIG. 8B, the distal member 90 of the actuator 190 comprises a cylindrical element 92 with an aperture 94 extending through its length. The aperture 94 is configured to receive the rotatable element 40 (FIGS. 4A-4C) and, more specifically, to receive the intermediate portion 45 of the rotatable element 40, enabling the cylindrical element 92 of the distal member 90 to slide, or move, along the length of the rotatable element 40, without engaging the rotation facilitator (e.g., the helical ridge 47, etc.) of the rotatable element 40.

The distal member 90 of the actuator 190 includes a pair of intermediate elements 98 protruding from opposite sides of the cylindrical element 92 and external elements 97 on the ends of the intermediate elements 98. The intermediate elements 98 of the distal member 90 are capable of being received by the longitudinal slot 34 through the housing 20 (FIG. 3A). The external elements 97 are capable of protruding from the housing 20 and being received by and coupling with corresponding features on a moveable element 102 of a handle 100 of the rooter 10 (FIGS. 1 and 2). Thus, the intermediate elements 98 and the external elements 97 of the distal member 90 of the actuator 190 enable movement of the distal member 90 of the actuator 190 along the length of the rotatable element 40 (FIGS. 4A-4C).

At its proximal end 91, the distal member 90 of the actuator 190 includes alignment features 99 and engagement features that comprise teeth 96. The alignment features 99 protrude beyond the proximal end 91 of the distal member 90 and are spaced apart and configured (e.g., tapered, etc.) to receive and align a proximal member 120 of the actuator 190 with the distal member 90. The teeth 96, which are formed in a proximal edge of the distal member 90, are configured to engage corresponding engagement features of the proximal member 120.

As illustrated by FIGS. 8A and 8G, as well as by FIGS. 8C-8F, those corresponding engagement features of the proximal member 120 of the actuator 190 comprise teeth 126 formed in a distal edge 129 of the proximal member 120. In addition to the teeth 126, the proximal member 120 includes a cylindrical element 122, an aperture 124 extending through the cylindrical element 122, and one or more drive features 125 formed in the surface of the aperture 124. In the specific embodiment shown in FIG. 8B, the drive features 125 may be configured to engage a corresponding rotation facilitator (e.g., the helical ridge 47, etc.) of the intermediate portion 45 of the rotatable element 40 (FIGS. 4A-4C). More specifically, the drive features 125 may engage the helical ridge 47 of the intermediate portion 45 of a rotatable element 40.

The teeth 126 of the proximal member 120 and the teeth 96 of the distal member 90 may be configured in such a way that the teeth 96 of the distal member 90 will engage the teeth 126 of the proximal member 120 as the distal member 90 is forced proximally, causing the rotatable element 45 to rotate in a first direction, or in a forward direction (e.g., clockwise), but enable the teeth 96 of the distal member 90 to disengage the teeth 126 of the proximal member 120 as the proximal member 120 is forced distally (e.g., by a return element 101 (FIGS. 1 and 10) and rotates in an opposite second direction, or in a reverse direction (e.g., counter-clockwise), such as when resistance on a device that has been coupled to the rotatable element 45 resists rotation in the second direction. In the illustrated embodiment, each tooth 96, 126 may include radially oriented drive surface and a somewhat circumferentially oriented slip surface that tapers outward from the base of one drive surface to the top of the next drive surface.

Figure 10:
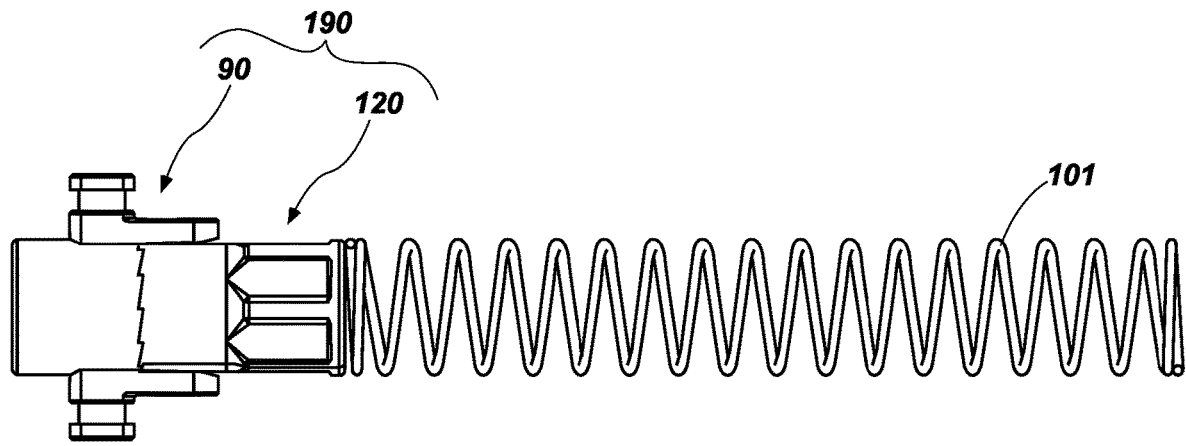
FIG. 10 shows the manner in which a biasing element is associated with the proximal member of the embodiment of actuator shown in FIG. 8A.
Figure 11:
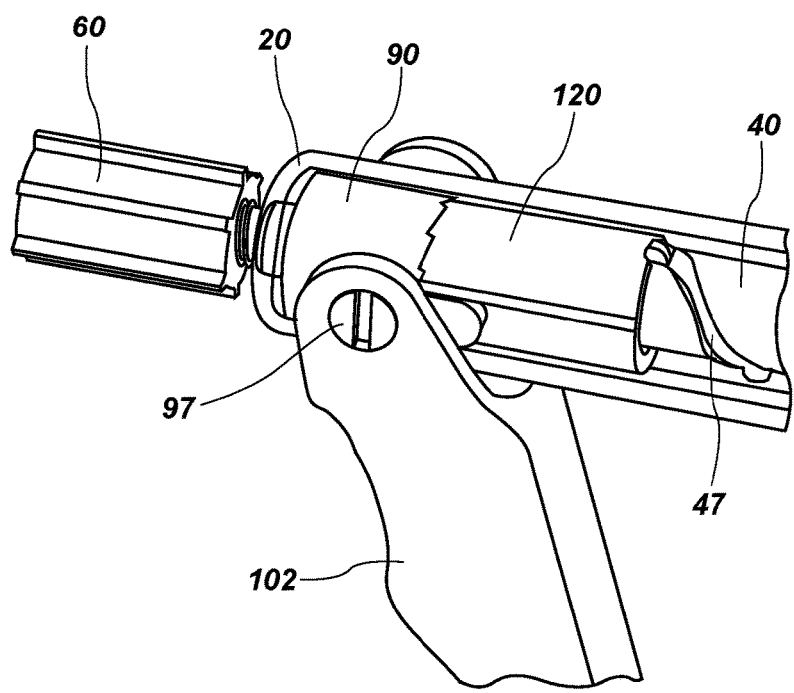
FIG. 11 provides a partial perspective cutaway view illustrating the embodiment of actuator shown in FIG. 8A in its starting position with the housing or a rooter.

In some embodiments, such as that depicted by FIG. 1, a rooter 10 that incorporates teachings may also include a return element 101, which is also referred to herein as a "biasing element," (e.g., a spring, etc.) that causes the actuator 190 (FIGS. 8A, 8G, 9, and 10) and the moveable element 102 of the handle 100 to return to or substantially to an initial position. When the moveable element 102 is moved in a first direction (e.g., proximally, etc.), energy may be stored in the return element 101. When the moveable element 102 is released, the resilience of the return element 101, and the energy stored within the return element 101, may cause the actuator 190 and the moveable element 102 of the handle 100 to move in an opposite, second direction (e.g., distally, etc.) along the lengths of the housing 20 and the rotatable element 40 of the rooter 10. As illustrated by FIG. 10, the return element 101 may comprise an internal compression spring, which, in the depicted embodiment, is compressed between a proximal edge 121 of the cylindrical element 122 of the proximal member 120 of the actuator 190 and an interior surface of the end 58 of the cap 56 as the moveable element 102 and, thus, the cylindrical element 122 of the proximal member 120 are force proximally along the rotatable element 40 and the housing 20. A distal end of the return element 101 abuts the proximal edge 121 of the cylindrical element 122 of the proximal member 120 of the actuator 190, while a proximal end of the return element 101 is held in place against the interior surface of the end 58 of the cap 56 (FIGS. 5A-5C). The return element 101 concentrically surrounds the rotatable element 40 of the rooter 10.

Return elements 101 that are centered around the rotatable element 40, such as the compression spring embodiments of the return element 101 shown in FIGS. 1 and 10, enable the cylindrical element 122 of the proximal member 120 of the actuator 190 to remain concentric or substantially concentric with the longitudinal axis 41 of the rotatable element 40. Thus, such a return element 101 prevents cocking of the actuator 190 relative to the rotatable element 40 and facilitates smooth strokes as the actuator 190 moves along the length of the rotatable element 40. Of course, a rooter 10 may also include other embodiments of return elements 101, including other types of internal springs, external springs (e.g., a torsion spring, which, in the embodiment depicted by FIG. 1, may be positioned between the moveable element 102 and the elongated handle 110 or equivalent features, etc.), the flexibility and resiliency of a connector 105 between bottom ends of the elongated handle 110 and the moveable element of the handle 100, and/or other apparatus that will cause the actuator 190 to automatically reverse its position.

The automatic return of the actuator 190 to its initial position may also cause the rotatable element 40 to rotate in its opposite direction, provided that any rotational resistance on a device that has been coupled to the coupling element 60 is not sufficient to overcome the biasing force of the return element 101. In the event that rotational resistance on the device is sufficient to overcome the biasing force of the return element 101, the proximal member 120 of the actuator 190 may disengage the distal member 90 of the actuator 190, enabling the distal member 90 to slide distally along the rotatable element 40 and the proximal member 120 to rotate freely relative to the rotatable element 40.

Returning reference to FIG. 2, assembly of a rooter 10 that includes the above-described elements may be accomplished by assembling the rotatable element 40 and the actuator 190. The distal portion 42 of the rotatable element 40 may be introduced into and through the apertures 94 and 124 of the cylindrical elements 92 and 122 of the distal member 90 and the proximal member 120 of the actuator 190. As the rotatable element 40 is pushed distally through the aperture 124 of the cylindrical element 122 of the proximal member 120, the drive features 125 of the proximal member 120 may engage the helical ridge 47 that protrudes from the outer surface 46 of the intermediate portion 45 of the rotatable element 40.

Assembly of the housing 50 and the actuator 190 may include introduction of the cylindrical elements 92 (FIGS. 8A and 8G) and 122 (FIGS. 8A and 8G) of the distal member 90 and the proximal member 120 of the actuator 190 into the opening 32 at the proximal end 30 of the housing 20, with the intermediate element(s) 98 of the distal member 90 of the actuator 190 located within the longitudinal slot(s) 34 through the housing 20. The moveable element 102 of the handle 100 is, of course, located outside of the housing 20, and protrudes from the housing 20.

The distal portion 42 of the rotatable element 40 may be introduced into the opening 32 at the proximal end 30 of the housing 20 to assemble the rotatable element 40 with the housing 20. The distal portion 42 of the rotatable element 40 is then moved distally through the interior 24 of the housing 20, until the distal portion 42 reaches the distal end 26 of the housing 20. The distal portion 42 of the rotatable element 40 may then be introduced into and through the opening 28 in the distal end 26 of the housing 20, until the distal portion 42 of the rotatable element 40 protrudes from the distal end 26 of the housing 20.

With the distal portion 42 of the rotatable element 40 protruding from the distal end 26 of the housing 20, the longitudinal position of the rotatable element 40 within the interior 24 of the housing 20 may be fixed or substantially fixed by coupling the distal retention element 60 to the distal portion 42 of the rotatable element 40.

When the housing 20 and the rotatable element 40 are assembled, the proximal portion 50 of the rotatable element 40 protrudes beyond the proximal end 30 of the housing 20. To hold the rotatable element 40 and the actuator 190 within the interior 24 of the housing 20, the cap 56 may then be placed over the proximal end 30 of the housing 20. More specifically, the receptacle 57 of the cap 56 may be positioned over the proximal end 30 of the housing 20. Additionally, the proximal portion 50 of the rotatable element 40 may be aligned with the aperture 59 through the end 58 of the cap 56. As the cap 56 moves distally relative to the housing 20 and the rotatable element 40, the proximal portion 50 of the rotatable element 40 may be positioned around proximal portion 50 of the rotatable element 40.

The cap 56 may be held in place relative to the proximal end 30 of the housing 20 by coupling the proximal retention element 70 to the protruding proximal portion 50 of the rotatable element 50.

Some embodiments of use of a rooter 10 according to this disclosure to rotate devices, such as elongated medical instruments, and to perform various procedures, including medical procedures, are disclosed. Since the rooter 10 may be configured to be used with a plurality of different types of devices, it provides a user (e.g., a healthcare provider, etc.) with a great deal of flexibility in selecting a specific device with which he or she prefers to perform a certain procedure.

In use, a proximal end of device that is to be rotated may be introduced into an opening 69 in the distal end 68 of the distal retention element 60 of the rooter 10. When the device comprises a relatively short device, insertion of the proximal end of the device into the opening 69 may at least partially couple the device to the rooter 10 without inserting the device further into the rooter 10. In embodiments where the device comprises a longer device, its proximal end may be inserted only into the opening 69 of the distal end 68 of the distal retention element 60, or the proximal end of the device may be inserted further into the rooter 10. Without limiting the scope of this disclosure, the proximal end of the device may also be pushed proximally through the conduit 55 of the rotatable element 40 of the rooter 10, and through the opening 79 through the proximal end 78 of the proximal retention element 70 of the rooter 10.

With the device in place, it may be rotationally coupled to the rooter 10. In embodiments where the distal retention element 60 and/or the proximal retention element 70 of the rooter 10 includes features that lock onto, grasp, or otherwise engage a surface of the device that is to be rotated, rotational coupling of the device to the rooter 10 occurs during assembly of the device with the rooter 10. In other embodiments, at least one separate locking device may be assembled with and lock onto, grasp, or otherwise engage the surface of the device that is to be rotated, and each locking device may be coupled to the distal retention element 60 or the proximal retention element 70 of the rooter 10. Rotational coupling of the device to the distal retention element 60 or the proximal retention element 70 may be effected in a manner that causes the device to rotate as the distal retention element 60 and/or the proximal retention element 70 rotates.

Rotation of the device (e.g., about its longitudinal axis, etc.) may be effected by causing the rotatable element 40, as well as the distal retention element 60 and/or the proximal retention element 70, to rotate (e.g., about longitudinal axis 41, etc.). In the illustrated embodiment, such rotation may be caused by moving the moveable element 102 of the handle 100 of the rooter 10 along the length of the housing 20 of the rooter 10. As the moveable element 102 is moved along the length of the housing 20, the intermediate element 98 of the distal member 90 of the actuator 190 moves through the longitudinal slot 34 in the housing 20, which causes the cylindrical element 92 of the distal member 90 of the actuator 190 within the interior 24 of the housing to move along the length of the rotatable element 40. As the cylindrical element 92 moves proximally along the length of the rotatable element 40, it forces the cylindrical element 122 of the proximal member 120 of the actuator 190 to move proximally along the length of the rotatable element 40. As the cylindrical element 122 moves proximally, drive features 125 (FIG. 8C) on or in the interior surface of the aperture 124 of the cylindrical element 122 may engage the complementarily configured rotation facilitator 47 of the rotatable element 40 (e.g., the depicted helical ridge, etc.). The configurations of the longitudinal slot 34 and the actuator 190 (specifically, the intermediate element(s) 98 of the distal member 90) may prevent rotation of the cylindrical element 92 of the distal member 90 within the interior 24 of the housing 20, or at least enable the rotatable element 40 to rotate relative to the housing 20. During rotation of the rotatable element 40, one or both of the distal retention element 60 and the proximal retention element 70 to rotate relative to the housing 20, which rotation may also cause the device that is to be rotated to spin relative to the housing 20 of the rooter 10. If the rooter 10 is held stationary, or at least substantially stationary, movement of the moveable element 102 of the handle 100 of the rooter 10 may cause the device to rotate or spin. In other embodiments, the rooter 10 may be used to rotationally oscillate the device, which may enhance the performance of the device. As an example, oscillation of a device may cause some vibration or quivering of the device, which may reduce friction during use of the device.

Rotation or oscillation of the device may be effected during or separately from longitudinal movement (e.g., distal movement, proximal movement, back-and-forth movement, etc.), or hammering movement, of the device. Conversely, hammering movement of a device may be effected with our without rotation or oscillation of the device.

When the proximal end of a tubular device is accessible from or proximally beyond the proximal end of the rooter 10 (e.g., beyond the proximal end 78 of the proximal retention element 70 of the rooter 10, etc.), other activities (e.g., aspiration, infusion, introduction of other elongated medical instruments, etc.) may be effected through the tubular device while it is assembled with the rooter 10 and, in some embodiments, as the tubular device is rotated, spun, or oscillated.

Although the foregoing description contains many specifics, these should not be construed as limiting the scope of any of the appended claims, but merely as providing information pertinent to some specific embodiments that may fall within the scopes of the disclosed subject matter the appended claims. Other embodiments may also be devised which lie within the scopes of the appended claims. Features from different embodiments may be employed in combination. The scope of each claim is, therefore, indicated and limited only by its plain language and the legal equivalents to the claim elements. All additions, deletions, and modifications to the disclosed subject matter that fall within the meaning and scopes of the claims are to be embraced thereby.

What is claimed:

1. A rooter, comprising:
   a rotatable element having a longitudinal axis and a length;
   an actuator, including:
      a first member movable along the length of the rotatable element and including a first side; and
      a second member movable along the length of the rotatable element and including a second side positionable against the first side of the first member, the second member having:
         an engaged arrangement in which the second member engages the first member in a manner that prevents rotation of the first member about the longitudinal axis of the rotatable element and enables the first member to rotate the rotatable element in a first direction and a second direction; and
         a disengaged arrangement in which the second member prevents the first member from rotating the rotatable element in the second direction by permitting the first member to rotate about the longitudinal axis of the rotatable element.

2. The rooter of claim 1, wherein the engaged arrangement of the second member of the actuator enables the first member to drive rotation of the rotatable element as the first member moves along the length of the rotatable element.

3. The rooter of claim 1, wherein the second member of the actuator can only be in the engaged arrangement when the second member pushes the first member of the actuator along the length of the rotatable element.

4. The rooter of claim 1, wherein the disengaged arrangement of the second member of the actuator enables the first member of the actuator to move along the length of the rotatable element without rotating the rotatable element.

5. The rooter of claim 3, wherein the disengaged arrangement of the second member of the actuator enables the first member of the actuator to move along the length of the rotatable element without rotating the rotatable element.

6. The rooter of claim 1, wherein the rotatable element includes a coupling element.

7. The rooter of claim 6, wherein the coupling element includes a medical device engagement feature.

8. A rooter, comprising:
   a rotatable element; and
   an actuator that causes the rotatable element to rotate, the actuator including:
      a second member that slides over the rotatable element without driving rotation of the rotatable element, the second member including a second side; and
      a first member that drives rotation of the rotatable element in a first direction and can drive rotation of the rotatable element in a second direction, the first member including a first side that can:
         engage the second side of the second member upon encountering less than a threshold resistance while rotating the rotatable element in the second direction to hold the second member rotationally stationary as the first member moves along the rotatable element to drive rotation of the rotatable element in the second direction,
         disengage the second side of the second member upon encountering at least the threshold resistance while rotating the rotatable element in the second direction to prevent the rotatable element from rotating in the second direction as the first member moves along the rotatable element by enabling the first member to rotate about the longitudinal axis of the rotatable element.

9. The rooter of claim 8, wherein the second member engages the first member as the second member is forced against the first member to hold the first member rotationally stationary and to enable the first member to drive rotation of the rotatable element in the first direction.

10. The rooter of claim 8, further comprising:
    a moveable element of a handle coupled to the second member of the actuator to force the second member over the length of the rotatable element and cause the second member to engage the first member to hold the first member rotationally stationary while forcing the first member over the length of the rotatable element to drive rotation of the rotatable element in the first direction.

11. The rooter of claim 8, further comprising:
a biasing member that exerts a longitudinally oriented force on the first member.

12. The rooter of claim 8, further comprising:
a biasing member that forces the first member along the length of the rotatable element.

13. The rooter of claim 12, wherein the biasing member comprises a coiled spring with:
a first end abutting a second side of the first member of the actuator,
an intermediate portion surrounding a portion of the rotatable element, and
a second end held at a fixed location.

14. The rooter of claim 8, wherein the second side of the second member of the actuator and the first side of the first member of the actuator comprise cooperating teeth.

15. The rooter of claim 14, wherein:
teeth of the second member of the actuator are arranged in a circle on the second side of the second member; and
teeth of the first member of the actuator are arranged in a circle on a first side of the first member.

16. The rooter of claim 15, wherein each tooth of the cooperating teeth includes:
a drive surface oriented radially to hold the first member of the actuator rotationally stationary when the second member of the actuator forces the first member along the rotatable element to drive rotation of the rotatable element in the first direction; and
a slip surface tapering outward from a base of the drive surface to enable the teeth of the first member to disengage the teeth of the second member to enable rotation of the first member about the rotatable element and movement of the first member along the rotatable element when the rotatable element resists rotation in the second direction.

17. The rooter of claim 8, further comprising:
a housing carrying the rotatable element.

18. A method for rotating an elongated medical device, comprising:
securing a proximal end of the elongated medical device to a coupling element of a manually operable rooter;
forcing a second member of an actuator of the manually operable rooter over a rotatable element of the manually operable rooter in a first direction without the second member rotationally driving the rotatable element;
causing the second member of the actuator to engage a first member of the actuator of the manually operable rooter in a manner that prevents the first member from rotating relative to the rotatable element, moves the first member over the rotatable element in the first direction, and enables to the first member to drive rotation of the rotatable element and rotation of the elongated medical device in a first rotational direction;
releasing a force on the second member of the actuator; and
forcing the first member of the actuator over the rotatable element in a second direction to enable the first member to rotate the rotatable element in a second rotational direction.

19. The method of claim 18, further comprising:
upon releasing the force on the second member of the actuator, disengaging the first member of the actuator from the second member of the actuator if the elongated medical device resists rotation in a second rotational direction opposite from the first rotational direction, enabling the first member to rotate about the rotatable element and to move along the rotatable element in the second direction without rotating the rotational element in the second rotational direction.

20. The method of claim 18, further comprising:
upon releasing the force on the second member of the actuator, maintaining engagement between the first member of the actuator and the second member of the actuator if the elongated medical device can rotate in the second rotational direction opposite from the first rotational direction, holding the first member rotationally stationary relative to the rotatable element, and causing the first member to move along the rotatable element in the second direction and drive rotation of the rotatable element in the second rotational direction.

* * * * *